(12) United States Patent
Rothenberg (10) Patent No.: US 8,457,965 B2
(45) Date of Patent: Jun. 4, 2013

(54) METHOD FOR THE CORRECTION OF MEASURED VALUES OF VOWEL NASALANCE

(75) Inventor: Martin Rothenberg, Jamesville, NY (US)

(73) Assignee: Rothenberg Enterprises, Jamesville, NY (US)

( * ) Notice: Subject to any disclaimer, the term of this patent is extended or adjusted under 35 U.S.C. 154(b) by 866 days.

(21) Appl. No.: 12/574,522

(22) Filed: Oct. 6, 2009

(65) Prior Publication Data

US 2011/0082697 A1    Apr. 7, 2011

(51) Int. Cl.
*G10L 15/02* (2006.01)
*G10L 15/06* (2006.01)
*G10L 17/00* (2006.01)
*G10L 15/00* (2006.01)

(52) U.S. Cl.
USPC ............................ 704/250; 704/244; 704/261

(58) Field of Classification Search
USPC ................ 704/1–10, 23–206, 207–209, 233, 704/236, 243–244, 246–250, 254, 261, 266, 704/268, E15.002–E15.05, E21.001–E21.02; 434/156–157, 167, 185
See application file for complete search history.

(56) References Cited

U.S. PATENT DOCUMENTS

| | | | |
|---|---|---|---|
| 3,752,929 A | | 8/1973 | Fletcher |
| 4,130,730 A * | 12/1978 | Ostrowski ..................... 704/264 |
| 4,335,276 A * | 6/1982 | Bull et al. ..................... 704/276 |
| 4,813,076 A * | 3/1989 | Miller .......................... 704/254 |
| 4,862,503 A * | 8/1989 | Rothenberg ................... 704/235 |
| 5,018,200 A * | 5/1991 | Ozawa .......................... 704/222 |
| 5,054,085 A * | 10/1991 | Meisel et al. ................. 704/207 |
| 5,454,375 A * | 10/1995 | Rothenberg ................... 600/538 |
| 5,617,507 A * | 4/1997 | Lee et al. ...................... 704/200 |
| 5,717,828 A * | 2/1998 | Rothenberg ................... 704/251 |
| 5,729,694 A * | 3/1998 | Holzrichter et al. ........... 705/17 |
| 6,006,175 A * | 12/1999 | Holzrichter ................... 704/208 |
| 6,134,529 A * | 10/2000 | Rothenberg ................... 704/270 |
| 6,151,571 A * | 11/2000 | Pertrushin ..................... 704/209 |
| 6,236,963 B1 * | 5/2001 | Naito et al. ................... 704/241 |
| 6,487,531 B1 * | 11/2002 | Tosaya et al. ................. 704/246 |
| 6,850,882 B1 | 2/2005 | Rothenberg |
| 6,974,424 B2 | 12/2005 | Fletcher et al. |
| 7,016,841 B2 * | 3/2006 | Kenmochi et al. ............ 704/258 |
| 7,266,497 B2 * | 9/2007 | Conkie et al. ................. 704/258 |

(Continued)

OTHER PUBLICATIONS

Spaienza et al. "Respiratory and Laryngeal Function Associated with Experimental Coupling of the Oral and Nasal Cavities." Cleft Palate-Craniofacial Journal. Mar. 1996, vol. 33 No. 2.*

(Continued)

*Primary Examiner* — Pierre-Louis Desir
*Assistant Examiner* — David Kovacek
(74) *Attorney, Agent, or Firm* — Morrison & Foerster LLP (57) ABSTRACT

A method is described for correcting and improving the functioning of certain devices for the diagnosis and treatment of speech that dynamically measure the functioning of the velum in the control of nasality during speech. The correction method uses an estimate of the vowel frequency spectrum to greatly reduce the variation of nasalance with the vowel being spoken, so as to result in a corrected value of nasalance that reflects with greater accuracy the degree of velar opening. Correction is also described for reducing the effect on nasalance values of energy from the oral and nasal channels crossing over into the other channel because of imperfect acoustic separation.

28 Claims, 3 Drawing Sheets

U.S. PATENT DOCUMENTS

| | | | |
|---|---|---|---|
| 2003/0023444 A1* | 1/2003 | St. John | 704/270.1 |
| 2004/0181396 A1* | 9/2004 | Lee et al. | 704/205 |
| 2006/0004567 A1* | 1/2006 | Russell | 704/209 |
| 2006/0045281 A1* | 3/2006 | Korneluk et al. | 381/60 |
| 2006/0212296 A1* | 9/2006 | Espy-Wilson et al. | 704/254 |
| 2009/0305203 A1* | 12/2009 | Okumura et al. | 434/185 |
| 2010/0235170 A1* | 9/2010 | Rothenberg | 704/270 |
| 2011/0082697 A1* | 4/2011 | Rothenberg | 704/244 |

OTHER PUBLICATIONS

Mayo et al. "Nasalance and Nasal Area Values: Cross-Racial Study." Cleft Palate-Craniofacial Journal. Mar. 1996, vol. 33 No. 2.*

Kendrick, Kathryn Ruth. "Nasalance Protocol Standardization: A Thesis." Louisiana State University: May 2004.*

Baken, R.J. and Orlikoff, R.F. (2000) "Velopharyngeal Function" Chapter 11 in *Clinical Measurement of Speech and Voice, Second Edition*, Singular, Thomson Learning, pp. 453-510.

Lewis, K. E. et al. (Nov. 2000) "The Effect Of Vowels On Nasalance Scores," *Cleft Palate-Craniofacial Journal*, 37(6): 584-589.

Gildersleeve-Neumann, E.E. and Dalston, R.M. (2001) "Nasalance Scores In Noncleft Individuals: Why Not Zero?" *Cleft Palate-Craniofacial Journal* 38(2): 106-111.

Nasalance System Model NAS-1 User Manual. Glottal Enterprises, Apr. 2009; 15 pages.

Zahorian, S.A. and Nossair, Z.B. (Jul. 1999) "A Partitioned Neural Network Approach for Vowel Classification Using Smoothed Time/Frequency Features," *IEEE Transactions on Speech and Audio Processing* 7(4): 414-425.

* cited by examiner

FIG. 6

METHOD FOR THE CORRECTION OF MEASURED VALUES OF VOWEL NASALANCE

BACKGROUND OF THE INVENTION

1. Field of the Invention

The invention relates to an improvement in a method and device for the diagnosis and treatment of speech disorders and more particularly to the dynamic measurement of the functioning of the velum in the control of nasality during speech.

2. Description of the Related Technology

A. Velar Control and Oronasal Valving in Speech.

During speech or singing, it is necessary to open and close the passageway connecting the oral pharynx with the nasal pharynx, depending on the specific speech sounds to be produced. This is accomplished by lowering and raising, respectively, the soft palate, or velum. Raising the velum puts it in contact with the posterior pharyngeal wall, to close the opening to the posterior nasal airflow passageway.

This oronasal (or velopharyngeal, as it is usually referred to in medical literature) passageway must be opened when producing nasal consonants, such as /m/ or /n/ in English, and is generally closed when producing consonants that require a pressure buildup in the oral cavity, such as /p/, /b/ or /s/. During vowels, and also the vowel-like sonorant consonants (such as /l/ or /r/ in English), the oronasal passageway must be closed or almost closed for a clear sound to be produced, though in some languages an appreciable oronasal opening during a vowel can have phonemic significance and thus be required for proper pronunciation. The first vowels in the words "francais" and "manger" in French are examples of such nasalized vowels. In addition, vowels adjoining a nasal consonant are most often produced with some degree of nasality during at least part of the vowel, especially if the vowel is between two nasal consonants (such as the vowel in "man" in English).

There are many disorders that result in inappropriate oronasal valving, usually in the form of a failure to sufficiently close the oronasal passageway during non-nasal consonants or non-nasalized vowels. Such disorders include cleft palate and repairs of a cleft palate, hearing loss sufficient to make the nasality of a vowel not perceptible to the speaker, and many neurological and developmental disorders. The effect on speech production of insufficient oronasal closure is usually separated into two effects, namely, the nasal escape of pressurized oral air, termed 'nasal emission', that limits oral pressure buildup in those speech sounds requiring an appreciable oral pressure buildup (as /p/, /b/, /s/ or /z/), and, secondly, the incomplete velar closure during vowels and sonorant consonants that is often referred to as 'nasalization'. (See R. J. Baken and R. F. Orlikoff, Clinical Measurement of Speech and Voice, second edition, 453 et seq. (Singular, Thomson Learning, 2000)). The terminology used here is that suggested by Baken and Orlikoff, supra, who also prefer to reserve the term 'nasality' for the resulting perceived quality of the voice.

Since the action of the velum is not easily observed and the acoustic effects of improper velar action are sometimes difficult to monitor auditorally, there is a need in the field of speech pathology for convenient and reliable systems to monitor velar action during speech, both to give the clinician a measure of such action and to provide a means of feedback for the person trying to improve velar control.

B. Previous Methods for Measuring Velar Function

The various methods for monitoring velar function according to the present art can generally be also divided into two categories, according to the aspect of nasality being measured: (a) those methods that measure velar control during consonants requiring an oral pressure buildup, and (b) those methods that measure velar control during vowels and sonorants. In this application, for brevity we hereafter use the term 'vowel' to refer to both vowels and sonorants (vowel-like consonants).

The field of the invention relates to a commonly used method for measuring the nasalization of vowels by recording the sound energies (either radiated acoustic pressure or radiated acoustic volume velocity, or airflow) separately emitted from the nose and mouth, usually in conjunction with the placing of a sound barrier held against the upper lip to improve the separation of the nasal and oral sounds, with microphones placed above and below the barrier, respectively. In U.S. Pat. Nos. 3,752,929 and 6,974,424, the nasal and oral energies are recorded in the form of the respective radiated acoustic pressures, while in U.S. Pat. No. 6,850,882, the nasal and oral sounds are recorded in the form of the respective volume velocities, using a two-chamber pneumotachograph mask having a separating membrane contacting the upper lip. The respective nasal and oral signals are suitably filtered and a ratio taken of the nasal to oral energies. This ratio is commonly referred to as vowel 'nasalance', and can be presented as either the Nasalance Ratio (nasal energy divided by oral energy) or Percent Nasalance (nasal energy divided by the sum of nasal and oral energies). The term 'nasalance' can be used to refer to either of these measures, or to any third measure mathematically derived by comparing oral and nasal acoustic energies.

Though nasalance is valuable as an objective measure of the degree of a lack of velar closure, in all methods for measuring vowel nasalance, there is a marked dependence of the value obtained on the vowel being spoken, even with the same degree of closure for each vowel. (Lewis K E, Watterson T and Quint T, "The effect of vowels on nasalance scores", Cleft Palate-Craniofacial Journal, 37: 584-589 (2000); Gildersleeve-Neumann, and Dalston, "Nasalance scores in non-cleft individuals: why not zero?" Cleft Palate-Craniofacial Journal, 38: 106-111 (2001)) This variation is presumed to be caused by the fact that for vowels having a constriction in the vocal tract anterior to the velum, there is a higher acoustic energy in the oral pharynx and thus a higher energy emitted nasally for the same degree of velar opening. Thus for a given velar opening, the vowel /i/ as in "bead" has a higher value of nasalance than the vowel /a/ as in "bob". For example, Baken and Orlikoff, supra, in their summary of the literature, report that the nasalance recorded for normal-speaking children according to the present art can vary from approximately 7% in a non-nasalized /a/ vowel to 17% in a non-nasalized /i/ vowel (with both vowels measured in a /p/ phonetic context that minimizes nasalization of the vowel). This range is consistent with the measurement in FIG. 5 below for an adult subject. This variation of 10% according to the vowel being spoken occurs even if there is no velar opening, since with no velopharyngeal opening there is still a small amount of nasally emitted energy that is caused by vibrations of the velar tissue, and this energy is apparently greater for the /i/ vowel.

Errors of 7% or 17% are quite significant in that the total range for the nasalance of vowels is much less than 100%. This range is theoretically from zero to only about 40%. Consequently, the nasalization of a specific vowel can be expected to raise its nasalance score by no more than about 30%, depending on the degree of nasalization (velar opening). The limitation on the total range for vowels can be better understood by considering that if the velum is fully lowered during a typical vowel, resulting in an unnaturally large degree of nasalization, the Percent Nasalance should be close to 50%, say between 40% and 60%, since there is roughly equal energy emitted from the oral and nasal passageways. (This assumes no abnormal constriction of the nasal passages, as may be evidenced with the swollen mucous membranes accompanying nasal congestion.) Values much above 50% would be expected only during nasal consonants, when the oral passageway is occluded. Thus, when a device for measuring nasalance is constructed according to the present art, the nasalance for a totally non-nasalized /i/vowel could be similar to that recorded for a moderately nasalized /a/ vowel.

In addition to the variation with the vowel spoken, nasalance values obtained using devices constructed according to the current art are affected by acoustic energy from one channel crossing over into the other channel because of an incomplete acoustic separation of the channels. Thus the lowest values of nasalance obtained tend to be about 5% to 7%, instead of near zero, as otherwise expected, and the values of nasalance recorded in properly articulated nasal consonants tend to vary from approximately 90% to 95%, instead of being closer to the theoretically expected 100%.

The variation of vowel nasalance according to the vowel spoken can be reduced somewhat by suitably filtering the oral and nasal signals or by using airflows instead of pressures as the variables to be measured, and the effect of acoustic crossover can be decreased by improving the acoustic separation means, however, none of these methods have shown the ability to eliminate or make negligible these distortion effects. In their comprehensive review of attempts to use nasalance as a measure of velar closure and nasality, Baken and Orlikoff, supra, p. 466, conclude that "It also remains unclear how nasalance is affected by the physical characteristics of the oral and nasal cavities . . . and by the phonetic demands of the spoken utterance." These authors review a number of attempts to devise testing procedures that circumvent, or at least take into account, the variability of the nasalance measure, by limiting testing to a fixed phonetic sequence, as a particular sentence, passage or nonsense syllable sequence.

SUMMARY OF THE INVENTION

It is a purpose of embodiments of the present invention to provide effective methods of and apparatus for significantly reducing the variation of recorded nasalance with the vowel being spoken, as well as for compensating for the acoustic energy crossing from one channel to the other because of incomplete acoustic separation of the channels. Nasalance measurements obtained according to embodiments of the invention better represent the degree of nasalization for all vowels, and could be effectively used with an arbitrary phonetic sequence in speech testing and training.

Methods for Identifying Vowels Spoken

In some embodiments of the methods and apparatus encompassed by the present invention, use is made of a computer program for the identification of the vowel being spoken. There are many such programs available, usually based on some partitioning of a multidimensional representation the frequency spectrum of the acoustic signal. One representative example has been presented by Zahorian and Nossair (A Partitioned Neural Network Approach for Vowel Classification Using Smoothed Time/Frequency Features, IEEE Transactions on Speech and Audio Processing, Vol. 7, No. 4, pp. 414-425, (1999)).

A method is described for correcting and improving the functioning of certain devices for the diagnosis and treatment of speech that dynamically measure the functioning of the velum in the control of nasality during speech. In said devices the respective oral and nasal components of the radiated acoustic energy during voiced speech sounds are physically separated and selectively compared to produce a measure of the nasalization that results from an incomplete velar closure between the oral and nasal cavities. This measure is generally termed nasalance. Previous systems for measuring nasalance do not accurately reflect the degree of velar closure in that the measure they provide can vary significantly with the vowel being spoken with the same degree of velar opening. The correction method described herein uses an estimate of the vowel frequency spectrum to greatly reduce the variation of nasalance with the vowel being spoken, so as to result in a corrected value of nasalance that reflects with greater accuracy the degree of velar opening. Correction is also described for reducing the effect on nasalance values of energy from the oral and nasal channels crossing over into the other channel because of imperfect acoustic separation.

It is an object of this invention to improve the utility of vowel nasalance measurement systems by correcting the nasalance reading for differences related to the articulation of the vowel being spoken.

It is a further object of this invention to correct a nasalance reading for the energy in one of the oral or nasal channels crossing over into the other channel because of incomplete acoustic separation of the channels.

In one embodiment of this invention, an estimate of the vowel being spoken is made is by measuring the frequency spectrum of the vowel being spoken, with the estimated vowel used to determine the proper correction of the nasalance reading.

In another embodiment of this invention, the patterns for various representative vowels are obtained from the user by having the user speak the vowels. In a preferred embodiment, the vowels are spoken in close conjunction with so-called pressure consonants, such as /b/ or /p/ in English that act to close the velopharyngeal pathway, so that the vowels recorded are non-nasalized or minimally nasalized.

In yet another embodiment of this invention, correction of the nasalance reading for incomplete acoustic separation of the respective nasal and oral channels is accomplished by subtracting from the energy recorded for each channel a percentage of the energy recorded for the other channel, before the calculation of nasalance is performed.

In yet another embodiment of this invention, correction of the nasalance reading for the vowel being spoken is accomplished by subtracting from the energy recorded for the nasal channel a proportion of the energy recorded for the oral channel, before the calculation of nasalance is performed, with the said proportion varying according to the vowel being spoken.

These, together with other objects, advantages, features and variants which will be subsequently apparent, reside in the details of the implementation of this method as more fully hereinafter described in the claims, with reference being had to the accompanying drawings forming a part thereof, wherein like numerals refer to like elements throughout.

DETAILED DESCRIPTION OF THE PREFERRED EMBODIMENTS

This invention is described in a preferred embodiment in the following description with reference to the Figures, in which like numbers represent the same or similar elements. While this invention is described in terms of one or more preferred embodiments, it will be appreciated by those skilled in the art that variations may be accomplished in view of these teachings without deviating from the spirit or scope of the present invention. For example, the present invention may be implemented using any combination of computer programming software, firmware or hardware. As a preparatory step, the computer programming code (whether software or firmware) will typically be stored in one or more machine readable storage devices such as fixed (hard) drives, diskettes, optical disks, magnetic tape, semiconductor memories such as ROMs, PROMs, etc. The apparatus including the computer programming code may be used by either executing the code directly from the storage device, by copying the code from the storage device into another storage device such as a hard disk, RAM, etc. or by transmitting the code on a network for remote execution. Methods according to the invention may be practiced by combining one or more machine readable storage devices containing the code according to the present invention with appropriate standard computer hardware to execute the code contained therein. An apparatus for practicing the invention may be one or more computers and storage systems containing or having network access to computer program(s) coded in accordance with the invention, and the method steps of the invention may be accomplished by routines, subroutines, or subparts of a computer program product.

Figure 1:
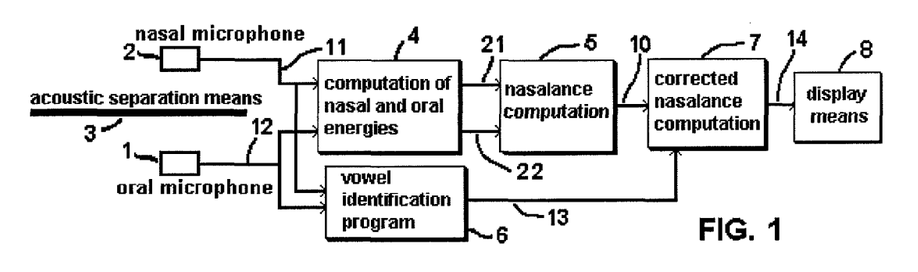
FIG. 1 is a diagrammatic representation of a system for measuring nasalance that employs a correction for the vowel spoken.

FIG. 1 illustrates an embodiment of the method for improving the measurement of voice nasalization described in this invention. In this figure, microphones 1 and 2 that record the oral and nasal acoustic energies, respectively, are separated acoustically by a separation means 3, which can be a partition resting against the upper lip or a mask that includes such a partition. The signals from these microphones, 11 and 12, are led to a computer program or other computation device 4 that computes numerical values of the nasal and oral voice energies, 21 and 22 respectively, in a manner known to those of skilled in the art as set forth in the publications mentioned earlier and cited at the end of this disclosure. From the energy measures 21 and 22, a calculation of nasalance 10 is made by computer program or other computation device 5, implemented and constructed according to, for example, the aforementioned publications and otherwise employing methods and techniques known by those skilled in the art. The oral microphone signal 12 and optionally the nasal microphone signal 11, or optionally the signal from a third microphone (not shown) that is placed so as to pick up both oral and nasal energy, are also entered into a computer program or other computation device 6 known to those skilled in the art that provides an estimate 13 of the vowel being spoken, which could be implemented in the manner described by Zahorian and Nassair (supra). The estimate 13 is provided to a computer program or other computation device 7 that computes a corrected value 14 for the nasalance from the original value 10. This corrected value 14 is input to a display device 8.

Figure 2:
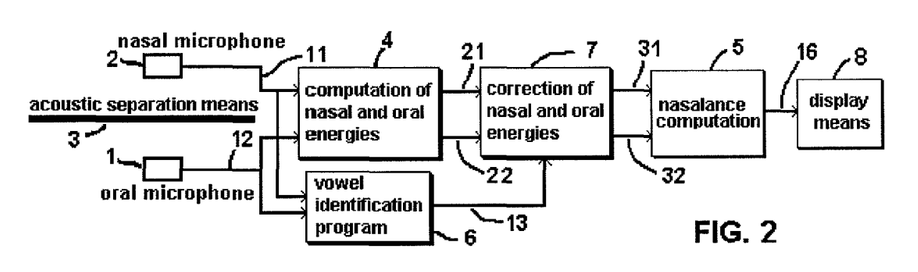
FIG. 2 is another diagrammatic representation of an alternative system for measuring nasalance that employs a correction for the vowel spoken.

FIG. 2 illustrates another embodiment of the method for improving the measurement of voice nasalization described in this invention. In this embodiment, using the output 13 of the vowel identification program 6, correction is made by a computer program or other computation device 7 to the measured nasal and oral acoustic energies 21 and 22, to produce corrected estimates of the nasal and oral energies, 31 and 32 respectively, before the nasalance estimate 16 is computed from these energies by the program 5.

Figure 3:
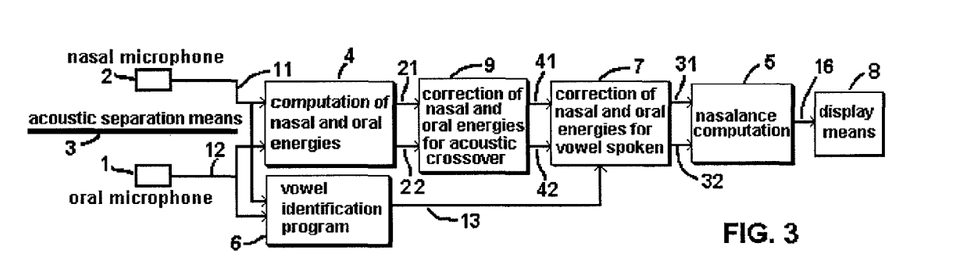
FIG. 3 is a diagrammatic representation of the system in FIG. 2 with provision added for correcting the nasalance values for acoustic crossover caused by inadequate acoustic separation between the nasal and oral channels.

FIG. 3 illustrates yet another embodiment of this invention in which there has been added a module 9 for the correcting for acoustic crossover between the nasal and oral channels caused by the imperfect acoustic separation of the channels. Modules 9, as may other functional systems and subsystems included in and/or implemented by various embodiments, may be implemented by software, hardware, firmware and/or any combination thereof. Module 9 may function to implement or cause a subtraction from the measured energy in each channel of a fixed percentage of the measured energy in the other channel. This program has as output estimates of the nasal energy 41 and oral energy 42 which are substantially corrected for the crossover of acoustic energy between the nasal and oral channels caused by imperfect acoustic separation, but are not corrected for the variations caused by the vowel being spoken. Correction for the vowel being spoken, if it is to be included in this embodiment, is performed by program 7, which has as input the energy estimates 41 and 42.

Figure 4:
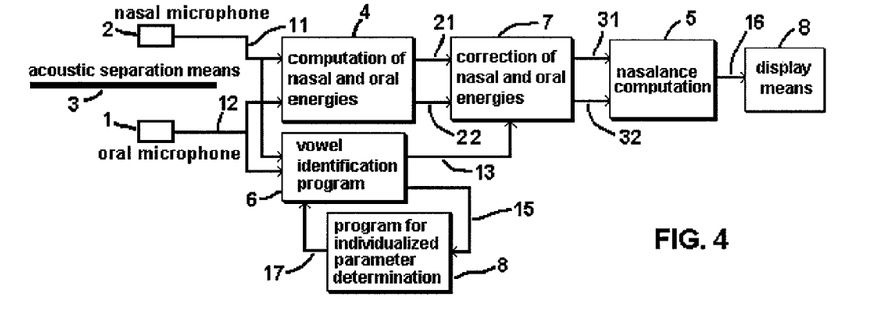
FIG. 4 is a diagrammatic representation of the system in FIG. 2 with provision added for individualizing the parameters of the vowel identification determination.

FIG. 4 illustrates another embodiment of the invention in which the parameters for the identification of a specific user's vowels are individualized for that user. In this embodiment, spectral parameters 15 that are used in the identification of the vowel by the program 6 are also output from the program 6. With the user speaking a predetermined vowel, these parameters are used by a program 8 to determine a set of individualized parameters 17 to be used in later testing by the vowel identification program 6 to output the correct identification of the vowel being spoken.

Figure 5:
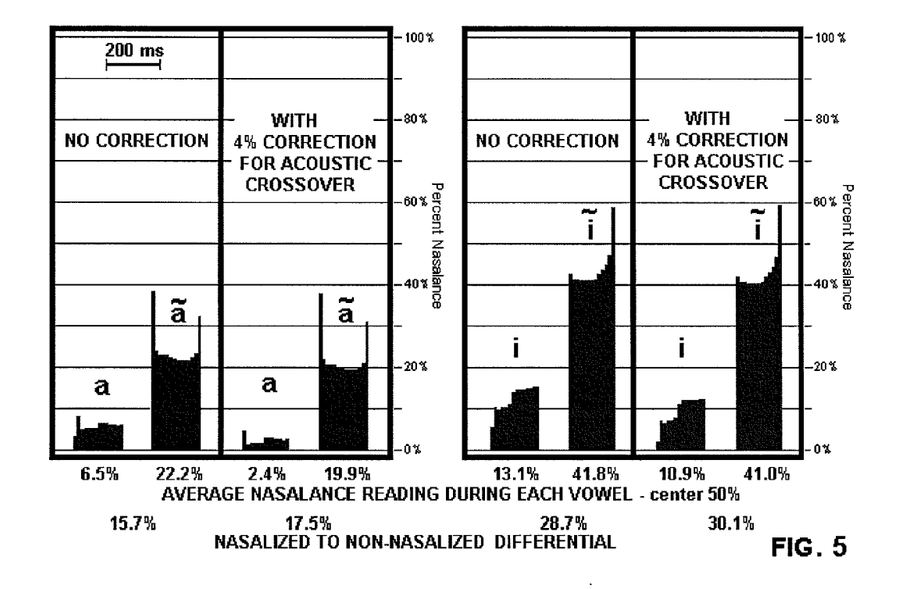
FIG. 5 shows nasalance measurements that illustrate the manner in which the method of FIG. 3 would correct nasalance values.

FIG. 5 illustrates the manner in which the method of FIG. 3 would correct nasalance values. The syllable sequence /pa-papa mamama pipipi mimimi/ was spoken by an adult male speaker with normal speech, and nasalance recorded using a mask-type separator for the oral and nasal energies. The system used for these nasalance measurements was the NAS system presently marketed by Glottal Enterprises (Nasalance System NAS-1 User Manual, supra). The vowels /a/ and /i/ were chosen because the /a/ vowel (as in "bob" or "bomb") and the /i/ vowel (as in "bee" or "bead") produce the least and the most, respectively, vowel-related nasal acoustic energy (Baken and Orlikoff, supra, Lewis and Watterson, supra, and Gildersleeve-Neumann and Dalston, supra)

The /p/ and /m/ consonant contexts for the vowels were chosen because for a speaker having normal articulation patterns, vowels between two /p/ consonants are produced with little or no nasalization, since the velopharyngeal passageway must be sealed to produce the oral pressure for the /p/ consonants, while between two /m/ consonants, the vowel is always produced nasalized because of coarticulation.

Shown in the FIG. 5 is the variation of nasalance for the middle syllable of each sequence of three syllables. Following standard phonetic notation, the nasalized vowels (spoken between the /m/ consonants) are labeled with a tilde (~) over the vowel syllable, while the non-nasalized vowels (between the /p/ consonants) have no tilde.

At left in each of the two panels of FIG. 5 is the nasalance as measured with no correction for acoustic crossover, that is, as measured by the unmodified commercial system constructed according to the present art. The average value of nasalance, measured in the central 50% of each vowel, for the vowels are approximately 6.5% for the non-nasalized /a/ and 13.1 percent for the non-nasalized /i/. The values for the nasalized variants of each vowel were 22.2% and 41.8%. These values agree with values reported in the literature for these vowels, including in the references cited in the present disclosure.

Note that if nasalance were to represent the degree of the velopharyngeal opening, the nasalance values for the non-nasalized vowels should be uniformly low, say below 3 or 4 percent.

To test the method for correcting for acoustic energy crossover, according to one embodiment, the analysis software was modified so as to subtract 4% of the nasal energy from the measured oral energy and 4% of the oral energy from the measured nasal energy. The value of 4% was selected to be slightly less than the values of 5% to 7% that might be predicted as optimum from the nasalance values cited in the literature (Baken and Orlikoff, supra, and Gildersleeve-Neumann and Dalston, supra). The resulting corrected values of nasalance are shown at right in each of the two panels of FIG. 5.

With a correction made for acoustic crossover between the oral and nasal channels, nasalance values were reduced to 2.4% for the non-nasalized /a/ vowel, and approximately 10.9% for non-nasalized /i/ vowel, an improvement, in both cases, in having the nasalance reflect the degree of velar closure. The differential in the nasalance values between nasalized and non-nasalized vowels of the same type was increased after correction, which is also an improvement. It can be noted that in both these measures, using a correction of slightly larger than 4%, say 5% or 6%, would yield further improvement.

Thus, for the vowel /a/, the corrected nasalance values reflect well the fact that there was no velar opening. However, further correction of the nasalance values for the /i/ vowels, to make them more similar to those for the /a/ vowels, would require the use of the additional correction for the vowel being spoken that is described in the application. In a possible implementation of this vowel-based correction, a percentage of the oral energy, dependent on the vowel, would be subtracted from the nasal energy, so as to reflect the degree to which additional nasal energy is forced by the vocal tract constriction anterior to the velum presented by the /i/. For example, if this percentage was chosen as 10% for the vowel /i/, a calculation of the resulting correction shows that the average corrected nasalance for the non-nasalized /i/ vowel would be reduced to 2.2%, clearly identifying it to be non-nasalized. The value for the nasalized vowel would go to 37.3% from 41.0%, with a differential of 35.1% between the nasal and non-nasal /i/ vowels. Correction could also be made by multiplying the computed nasalance value by a correction factor related to the vowel determination.

Figure 6:
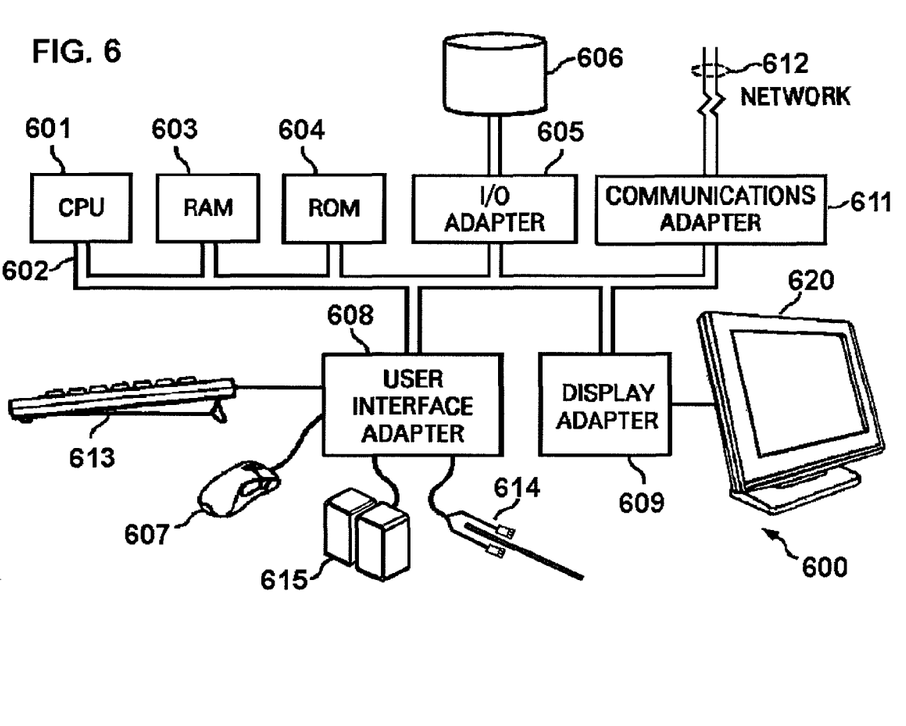
FIG. 6 is a block diagram of a computer platform for executing computer program code implementing processes and steps according to various embodiments of the invention.

FIG. 6 is a block diagram of a computer platform for executing computer program code implementing processes and steps according to various embodiments of the invention. Object processing and database searching may be performed by computer system 600 in which central processing unit (CPU) 601 is coupled to system bus 602. CPU 601 may be any general purpose CPU. The present invention is not restricted by the architecture of CPU 601 (or other components of exemplary system 600) as long as CPU 601 (and other components of system 600) supports the inventive operations as described herein. CPU 601 may execute the various logical instructions according to embodiments of the present invention. For example, CPU 601 may execute machine-level instructions according to the exemplary operational flows described above in conjunction with FIGS. 1 and 2.

Computer system 600 also preferably includes random access memory (RAM) 603, which may be SRAM, DRAM, SDRAM, or the like. Computer system 600 preferably includes read-only memory (ROM) 604 which may be PROM, EPROM, EEPROM, or the like. RAM 603 and ROM 604 hold/store user and system data and programs, such as a machine-readable and/or executable program of instructions for object extraction and/or video indexing according to embodiments of the present invention.

Computer system 600 also preferably includes input/output (I/O) adapter 605, communications adapter 611, user interface adapter 608, and display adapter 609. I/O adapter 605, user interface adapter 608, and/or communications adapter 611 may, in certain embodiments, enable a user to interact with computer system 600 in order to input information.

I/O adapter 605 preferably connects to storage device(s) 606, such as one or more of hard drive, compact disc (CD) drive, floppy disk drive, tape drive, etc. to computer system 600. The storage devices may be utilized when RAM 603 is insufficient for the memory requirements associated with storing data for operations of the system (e.g., storage of videos and related information). Although RAM 603, ROM 604 and/or storage device(s) 606 may include media suitable for storing a program of instructions for video process, object extraction and/or video indexing according to embodiments of the present invention, those having removable media may also be used to load the program and/or bulk data such as large video files.

Communications adapter 611 is preferably adapted to couple computer system 600 to network 612, which may enable information to be input to and/or output from system 600 via such network 612 (e.g., the Internet or other wide-area network, a local-area network, a public or private switched telephony network, a wireless network, any combination of the foregoing). For instance, users identifying or otherwise supplying a video for processing may remotely input access information or video files to system 600 via network 612 from a remote computer. User interface adapter 608 couples user input devices, such as keyboard 613, pointing device 607, and the dual microphone with acoustic separator required for nasalance measurement 614, and output devices, such as speaker(s) 615, to computer system 600. Display adapter 609 is driven by CPU 601 to control the display on display device 610 to, for example, display information regarding a video being processed and providing for interaction of a local user or system operator during object extraction and/or video indexing operations.

It shall be appreciated that the present invention is not limited to the architecture of system 600. For example, any suitable processor-based device may be utilized, including without limitation personal computers, laptop computers, computer workstations, and multi-processor servers. Moreover, embodiments of the present invention may be implemented on application specific integrated circuits (ASICs) or very large scale integrated (VLSI) circuits. In fact, persons of ordinary skill in the art may utilize any number of suitable structures capable of executing logical operations according to the embodiments of the present invention.

The illustrated embodiments are shown by way of example. The spirit and scope of the invention is not restricted by the preferred embodiments shown. Thus, it is to be understood that the invention is capable of use in various combinations and environments and is capable of changes or modifications within the scope of the inventive concept as expressed herein.

It should also be noted and understood that all publications, patents and patent applications mentioned in this specification are indicative of the level of skill in the art to which the invention pertains. All publications, patents and patent applications are herein incorporated by reference to the same extent as if each individual publication, patent or patent application was specifically and individually indicated to be incorporated by reference in its entirety.

PUBLICATIONS CITED

| U.S. Patent Documents | | |
|---|---|---|
| 3,752,929 | August 1973 | Fletcher |
| 6,850,882 | February 2005 | Rothenberg |
| 6,974,424 | December 2005 | Fletcher |

Non-Patent Publications

Baken, R. J. and Orlikoff, R. F., Clinical Measurement of Speech and Voice, second edition, Chapter 11, Velopharyngeal Function, pp. 453-510 (Singular, Thomson Learning, 2000)

Lewis, K E, Watterson, T and Quint, T, "The effect of vowels on nasalance scores", Cleft Palate-Craniofacial Journal, 37: 584-589 (2000)).

Gildersleeve-Neumann, E. E. and Dalston, R. M . . . "Nasalance scores in noncleft individuals: why not zero?" Cleft Palate-Craniofacial Journal, 38 (2), pp. 106-111, 2001.

Nasalance System Model NAS-1 User Manual. Glottal Enterprises, April, 2009

Zahorian, S. A. and Nossair, Z. B., "A Partitioned Neural Network Approach for Vowel Classification Using Smoothed Time/Frequency Features," IEEE Transactions on Speech and Audio Processing, Vol. 7, No. 4, pp. 414-425, July, 1999.

What is claimed is:

1. A method for correcting recorded values of vowel 'nasalance', comprising:
    computing a measure of speech nasalization from respective nasally and orally emitted acoustic energies, wherein the corrected values reflect more closely the degree of opening of a velopharyngeal passageway between the oral pharynx and the nasal pharynx, and
    wherein the recorded values of nasalance are substantially corrected by a processor for energy in the respective oral and nasal channels that crosses over into the other channel because of an incomplete acoustic separation of the channels.

2. The method according to claim 1 in which the variation of nasalance with the vowel being spoken is substantially reduced.

3. The method of claim 2 further comprising a measurement of the frequency spectrum of the vowel being spoken, with said measurement used to reduce the variation of nasalance according to the vowel being spoken.

4. The method in claim 3 in which the correcting of vowel nasalance is implemented by correcting the recorded values of nasal and oral acoustic energy according to the vowel being spoken.

5. The method according to claim 3 wherein the correction method uses patterns of the frequency spectrum for a number of representative vowels that are obtained for each user by having the user record these vowels in a consonant context that results in a complete velar closure.

6. The method according to claim 1 wherein the correction is implemented by subtracting from each channel's recorded energy a fixed proportion of the energy recorded in the other channel.

7. A method of correcting recorded values of vowel nasalance comprising:
    providing an acoustic separation between nasal and oral passageway openings of a subject;
    separately detecting nasal and oral acoustic energies emitted by the subject;
    correcting for crossover energy between the nasal and oral acoustic energies;
    computing vowel nasalance values based on the nasal and oral acoustic energies; and
    displaying the computed vowel nasalance values, wherein said step of correcting includes:
        subtracting a portion of a value of the detected nasal acoustic energy from a value of the detected oral acoustic energy to provide a corrected oral acoustic energy; and
        subtracting a portion of a value of the detected oral acoustic energy from a value of the detected nasal acoustic energy to provide a corrected nasal acoustic energy.

8. The method according to claim 7 further comprising identifying a vowel spoken by the subject and, in response, correcting for the crossover energy between the nasal and oral acoustic energies.

9. The method according to claim 8 wherein the step of identifying a vowel spoken by the subject includes identifying sounds having different vowel-related acoustic energies.

10. The method according to claim 8 wherein the step of correcting includes subtracting a portion of a value of the detected oral acoustic energy from a value of the detected nasal acoustic energy to provide a corrected nasal acoustic energy, the portion responsive to the vowel spoken by the subject.

11. The method according to claim 7 wherein the step of correcting includes multiplying the computed value of nasalance by a correction factor, the factor responsive to the vowel spoken by the subject.

12. An apparatus for measuring nasalance of a speech of a subject comprising:
    an acoustic barrier configured to provide acoustic separation between nasal and oral passageways of a subject;
    nasal and oral acoustic transducers for providing respective nasal and oral signals indicative of nasal and oral acoustic sounds emitted by the subject during speech; and
    a processor configured to:
        compute, in response to the nasal and oral signals, nasal and oral acoustic energy levels emitted by the subject;
        correct for crossover energy between the nasal and oral acoustic energy levels;
        compute vowel nasalance values based on the nasal and oral acoustic energy levels; and
        display the computed vowel nasalance values,
    wherein the processor is further configured to:

subtract a portion of the nasal acoustic energy level from the oral acoustic energy level to provide a corrected oral acoustic energy level; and subtract a portion of a value of the oral acoustic energy level from the nasal acoustic energy level to provide a corrected nasal acoustic energy level.

13. The apparatus according to claim 12 wherein the processor is further configured to identify a vowel spoken by the subject and, in response, correct for the crossover energy between the nasal and oral acoustic energy levels.

14. The apparatus according to claim 13 wherein the processor is further configured to subtract a portion a portion of the oral acoustic energy level from the nasal acoustic energy level to provide the corrected nasal acoustic energy level, the portion responsive to the vowel spoken by the subject.

15. The apparatus according to claim 13 wherein the processor is further configured to multiply the computed value of nasalance by a correction factor, the factor responsive to the vowel spoken by the subject.

16. The apparatus according to claim 13 wherein the identifying of a vowel spoken by the subject includes identifying sounds having different vowel-related acoustic energies.

17. A method for correcting recorded values of vowel 'nasalance', comprising:

computing a measure of speech nasalization from respective nasally and orally emitted acoustic energies, wherein the corrected values reflect more closely the degree of opening of a velopharyngeal passageway between the oral pharynx and the nasal pharynx, and wherein the variation of nasalance with the vowel being spoken is substantially reduced, wherein the correction is implemented by a processor by subtracting from the nasal channel's recorded energy a proportion of the energy recorded in the oral channel, the proportion varying according to the vowel being spoken.

18. The method according to claim 17 in which recorded values of nasalance are substantially corrected for energy in the respective oral and nasal channels that crosses over into the other channel because of an incomplete acoustic separation of the channels.

19. The method according to claim 18 wherein the correction is implemented by subtracting from each channel's recorded energy a fixed proportion of the energy recorded in the other channel.

20. The method of claim 17 further comprising a measurement of the frequency spectrum of the vowel being spoken, with said measurement used to reduce the variation of nasalance according to the vowel being spoken.

21. The method in claim 20 in which the correcting of vowel nasalance is implemented by correcting the recorded values of nasal and oral acoustic energy according to the vowel being spoken.

22. The method according to claim 20 wherein the correction method uses patterns of the frequency spectrum for a number of representative vowels that are obtained for each user by having the user record these vowels in a consonant context that results in a complete velar closure.

23. A method of correcting recorded values of vowel nasalance comprising:

providing an acoustic separation between nasal and oral passageway openings of a subject;

separately detecting nasal and oral acoustic energies emitted by the subject;

correcting for crossover energy between the nasal and oral acoustic energies;

computing vowel nasalance values based on the nasal and oral acoustic energies; and displaying the computed vowel nasalance values, the method further comprising identifying a vowel spoken by the subject and, in response, correcting for the crossover energy between the nasal and oral acoustic energies, wherein the step of correcting includes subtracting a portion of a value of the detected oral acoustic energy from a value of the detected nasal acoustic energy to provide a corrected nasal acoustic energy, the portion responsive to the vowel spoken by the subject.

24. The method according to claim 23 wherein the step of identifying a vowel spoken by the subject includes identifying sounds having different vowel-related acoustic energies.

25. The method according to claim 23 wherein the step of correcting includes multiplying the computed value of nasalance by a correction factor, the factor responsive to the vowel spoken by the subject.

26. An apparatus for measuring nasalance of a speech of a subject comprising:

an acoustic barrier configured to provide acoustic separation between nasal and oral passageways of a subject;

nasal and oral acoustic transducers for providing respective nasal and oral signals indicative of nasal and oral acoustic sounds emitted by the subject during speech; and a processor configured to:

compute, in response to the nasal and oral signals, nasal and oral acoustic energy levels emitted by the subject;

correct for crossover energy between the nasal and oral acoustic energy levels;

compute vowel nasalance values based on the nasal and oral acoustic energy levels; and display the computed vowel nasalance values, wherein the processor is further configured to identify a vowel spoken by the subject and, in response, correct for the crossover energy between the nasal and oral acoustic energy levels, and wherein the processor is further configured to subtract a portion a portion of the oral acoustic energy level from the nasal acoustic energy level to provide the corrected nasal acoustic energy level, the portion responsive to the vowel spoken by the subject.

27. The apparatus according to claim 26 wherein the processor is further configured to multiply the computed value of nasalance by a correction factor, the factor responsive to the vowel spoken by the subject.

28. The apparatus according to claim 26 wherein the identifying of a vowel spoken by the subject includes identifying sounds having different vowel-related acoustic energies.

* * * * *